United States Patent [19]

Hodge et al.

[11] Patent Number: 4,966,723

[45] Date of Patent: Oct. 30, 1990

[54] BLEACH ACTIVATORS IN DETERGENT COMPOSITIONS

[75] Inventors: Stephen R. Hodge, Kirkella; Andrew Pearce, Brough, both of England

[73] Assignee: BP Chemicals Limited, London, England

[21] Appl. No.: 401,443

[22] PCT Filed: Feb. 9, 1989

[86] PCT No.: PCT/GB89/00130

§ 371 Date: Sep. 14, 1989

§ 102(e) Date: Sep. 14, 1989

[87] PCT Pub. No.: WO89/07639

PCT Pub. Date: Aug. 24, 1989

[30] Foreign Application Priority Data

Feb. 11, 1988 [GB] United Kingdom ............... 8803114

[51] Int. Cl.$^5$ .......................... C11D 3/28; C11D 3/39
[52] U.S. Cl. ...................... 252/102; 252/95; 252/99; 252/186.4; 252/186.41
[58] Field of Search ............... 252/95, 99, 102, 186.4, 252/186.41

[56] References Cited

U.S. PATENT DOCUMENTS

| 3,775,333 | 11/1973 | Loffelman et al. | 252/99 |
| 3,840,466 | 10/1974 | Gray | 252/99 |
| 3,850,920 | 11/1974 | Walles | 252/102 |
| 3,928,223 | 12/1975 | Murray | 252/95 |
| 4,147,654 | 4/1979 | Rapko | 252/186.4 |
| 4,271,031 | 6/1981 | Oppenlaender et al. | 252/156 |
| 4,551,263 | 11/1985 | Schellhammer et al. | 252/186.39 |

FOREIGN PATENT DOCUMENTS 2205867 12/1988 United Kingdom .

Primary Examiner—Prince E. Willis
Attorney, Agent, or Firm—Brooks Haidt Haffner & Delahunty

[57] ABSTRACT

The present invention relates to a detergent composition in aqueous solution comprising:
(i) a surfactant selected from anionic, nonionic, zwitterionic and cationic surfactants and mixtures thereof,
(ii) a precursor compound capable of giving rise to a peroxygen compound in the presence of water,
(iii) a bleach activator capable of enhancing the bleaching activity of the peroxygen compound so formed,
(iv) a suds suppressing agent and
(v) a detergent building, characterised in that the bleach activator comprises one or more cyclic tertiary nitrogen compounds of a defined generic formula, said activator being at least partially soluble in water.

The claimed bleach activators show bleaching activity at relatively low temperatures.

21 Claims, No Drawings

BLEACH ACTIVATORS IN DETERGENT COMPOSITIONS

The present invention relates to the use of bleach activators, especially in detergent compositions.

Compounds such as tetraacetyl ethylene diamine (hereafter referred to as "TAED") are well known. Processes for the production of such compounds are disclosed for instance in published German patent application No. 2832021. These compounds are said to be efficient in activating the conventional inorganic salts used as bleach precursors in detergent compositions and generate peracetic acid in situ by the reaction thereof with alkaline hydrogen peroxide. The activating agent for the bleach precursor is the so-called bleach activator. Specific examples of such bleach precursors are sodium perborate and sodium percarbonate. In the absence of the activators the bleach precursor is satisfactorily effective only at elevated temperatures, its effectiveness being very slow at lower temperatures. The use of compounds such as TAED enable the bleach precursor to function more effectively at temperatures of the order of 60° C.

It has now been found that certain cyclic nitrogen compounds function efficiently as additives in activating the bleach precursor in detergent compositions, especially at low temperatures.

Accordingly the present invention is a detergent composition in aqueous solution comprising:

(i) a surfactant selected from anionic, nonionic, zwitterionic and cationic surfactants and mixtures thereof, (ii) a precursor compound capable of giving rise to a peroxygen compound in the presence of water, (iii) a bleach activator capable of enhancing the bleaching activity of the peroxygen compound so formed, (iv) a suds suppressing agent and (v) a detergent builder, characterised in that the bleach activator comprises one or more cyclic tertiary nitrogen compounds of the generic formula

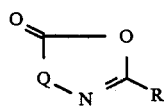

(I)

wherein Q is an organic divalent grouping such that Q and N together with the carbonyl and oxygen functions in the compound form one or more cyclic structures, and R is H, an alkyl, alkaryl, aryl, aralkyl, alkoxyl, haloalkyl, amino, amino alkyl, carboxylic or a carbonyl-containing function, said activator being at least partially soluble in water.

Where R has an aryl, alkaryl or aralkyl containing function, it is essential that such functions also carry a substituent capable of solubilising the activator in aqueous systems e.g. a sulphonic acid group. Where R is a halogen containing function the halogen is preferably chlorine or bromine Examples of such compounds include:

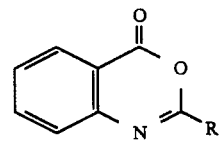

(II)

wherein R has the same significance as in formula (I) above. A specific example of such a compound (R=CH$_3$) is 2-methyl-(4H)3,1-benzoxazin-4-one.

Other compounds of this type include those in which R= an alkylamino group e.g. dimethylamino group; an acyl group e.g. a CH$_3$.CO group; an alkoxyl group e.g. ethoxyl group; a haloalkyl group e.g. a chloro-methyl, a dichloromethyl or a trichloromethyl group; an alkoxyalkylene ether group, e.g. a methoxy methylene ether group; or, an alkylene carboxylate group e.g. a —(CH$_2$)$_2$ COO— group.

Another compound of this type is shown in formula (III) below:

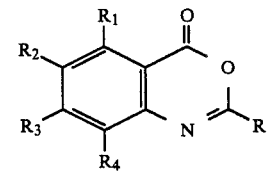

(III)

wherein R has the same significance as in formula (I) above, and R$_1$, R$_2$, R$_3$ and R$_4$ may be the same or different nuclear substituents and may be selected from H, halogen, alkyl, alkenyl, aryl, hydroxyl, alkoxyl, amino, alkyl amino, COOR$_5$ (where R$_5$ is an H or an alkyl group), and carbonyl functions. Specific examples of compounds of this type include those in which: (a) R$_1$ and R$_4$ are both H, and R$_3$=H and R$_2$=OH; R$_2$=acetoxy and R$_3$=H; R$_2$=R$_3$=alkoxy, especially methoxy; R$_2$=H but R$_3$= a halogen or a haloalkyl e.g. chlorine group or a chloromethylene group; R$_2$=halogen or haloalkyl group and R$_3$=H; and (b) either R$_1$, R$_2$ or R$_4$=alkyl e.g. methyl but the others are all H.

A further compound of this type is shown in formula (IV) below:

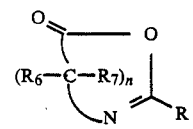

(IV)

where R has the same significance as in formula (I) above, R$_6$ and R$_7$ may be the same or different groups and may be any one of the groups denoted by the substituents R$_1$ to R$_4$ above, and n has a value from 1-3.

Again, the cyclic tertiary nitrogen compound may be of the formula (V) shown below:

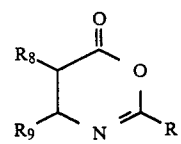

(V)

wherein R has the same significance as in formula (I) above and R$_8$ and R$_9$ are the same or different groups and may be any one of the groups listed in the context of $R_1-R_4$ above. A specific example of a compound of this type is where $R_8$ and $R_9$ together represent one or more benzene rings as in formula (II) above, or, where they together with the two hydrocarbyl carbon atoms bridging the nitrogen and carbonyl functions represent a pyrazole, pyrimidine, pyridine, pyridazine or an imidazole ring.

Similarly bleach activators of the present invention may have the formulae (VI) or (VII) below:

 (VI)

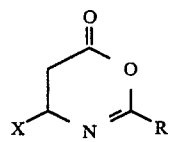 (VII)

wherein R has the same significance as in formula (I) above and X is H or an organic monovalent group. A specific example of a compound shown in formula (VII) above is where $X=CH_3$ and $R=Ph$.

Compounds of formula (II) above can be synthesised by acylation of isatoic anhydride with an anhydride. For instance, where $R=CH_3$, the acylating agent is acetic anhydride. The compounds of structures (VI) and (VII) can be synthesised from the corresponding alpha- or beta- amino acid respectively.

Alternatively, the tertiary nitrogen compound may be prepared by acylation of an amino acid as follows:

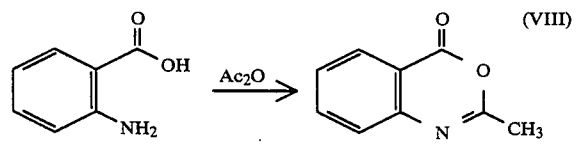 (VIII)

A further example of such a compound is

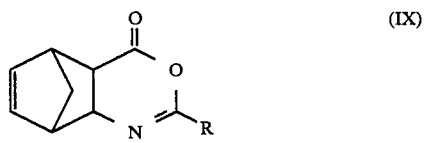 (IX)

wherein R has the same significance as in formula (I) above.

The bleach activator is at least partially soluble in water. Thus the solubility is at least 0.01% w/w in water at ambient temperature, e.g. 25° C.

It is believed that the activators of the present invention preferentially react with the peroxygen compound, e.g. hydrogen peroxide generated by contacting the precursor compound with water. This is believed to result in a peroxygen species of enhanced bleaching activity than that initially generated.

The bleach activators of the present invention can be used as such or in conjunction with other conventional activators such as TAED, phthalic anhydride, maleic anhydride, succinic anhydride isononanoyl oxybenzene sulphonate (also known as isonobs') and tetracetyl glycoluril (also known as "TAGU") and the like or with mixtures of such known activators.

Any of the well known surfactants can be used in the detergent compositions of the present invention. A typical list of these surfactants can be found in EP No. 0120591 and in U.S. Pat. No. 3,663,961.

Examples of water soluble anionic surfactants include the salts of alkyl benzene sulphonates, paraffin sulphonates, alpha-olefin sulphonates, alkyl glyceryl ether sulphonates and 2-acyloxy alkane-1-sulphonate, and beta-alkyloxy alkane sulphonate. Similarly, salts of alkyl sulphates, alkyl polyalkoxy ether sulphates, alpha-sulpho-carboxylates and their esters, fatty acid monoglyceride sulphates and sulphonates and alkyl phenol polyalkoxy ether sulphates may also be used.

Suitable examples of the above surfactants are linear straight chain alkyl benzene sulphonates having alkyl groups with 8–16 carbon atoms and methyl branched alkyl sulphates having 8–16 carbon atoms which are also effective.

Other anionic detergent compounds suitable for use herein include the sodium alkyl glyceryl ether sulphonates derived from tallow and coconut oil; sodium fatty acid monoglyceride sulphonates and sulphates derived from coconut oil; and sodium or potassium salts of $C_8-C_{12}$ alkyl phenol alkylene oxide ether sulphate containing up to 10 alkylene oxide units per molecule. Mixtures of anionic surfactants may also be used.

A substantial list of such compounds can be found in e.g. McCutcheon's Dictionary of Emulsifiers and Detergents, International Edition (1981), published by the Manufacturing Confectioner Publishing Co. and in "Surfactants Europa: A Directory of Surface Active Agents available in Europe", Ed. Gordon L. Hollis, Vol 1 (1982), published by George Goodwin.

The nonionic surfactants which may be used in the present invention are condensates of an alkylene oxide e.g. ethylene oxide with a hydrophobic group to form a surfactant having an appropriate hydrophilic-lipophilic balance (HLB) in the range from 8 to 17, suitably from 9.5 to 13.5, preferably from 10 to 12.5. The hydrophobic group may be an aliphatic or aromatic type and the length of the polyoxyethylene group condensed therewith can be readily adjusted to yield a water-soluble compound having the desired degree of HLB.

Examples of suitable nonionic surfactants include:
(a) The polyethylene oxide condensates of alkyl phenol in which the alkyl group e.g. contains from 6 to 12 carbon atoms and in which from 3 to 30 moles, preferably 5 to 14 moles of ethylene oxide are present. Other examples include a mole of dodecylphenol condensed with 9 moles of ethylene oxide, a mole of dinonylphenol condensed with 11 moles of ethylene oxide and a mole of nonylphenol and octadecylphenol condensed with 13 moles of ethylene oxide.
(b) The nonionic surfactant may also be formed as a condensation product of a mole of primary or secondary $C_8-C_{24}$ aliphatic alcohols with from 2 to 40 moles, preferably 2 to 9 moles of ethylene oxide.

Specific examples of nonionic surfactants useful for the purposes of the invention include the various grades of Dobanol (Registered Trade Mark, supplied by Shell) Lutensol (Registered Trade Mark, supplied by BASF) and Synperonics (Registered Trade Mark, supplied by ICI).

Other useful nonionic surfactants include the synthetic nonionic detergents available on the market under "Pluronics" (Registered Trade Mark) and supplied by Wyandotte Chemicals Corporation.

Zwitterionic compounds such as betaines and sulphobetaines, particularly those with a $C_8$–$C_{16}$ alkyl substituent on the nitrogen atom can also be used as surfactants. Examples of cationic surfactants that can be used include e.g. quaternary ammonium surfactants and surfactants of a semi-polar nature, for example amine oxides. Suitable quaternary ammonium surfactants are the mono $C_8$–$C_{16}$, N-alkyl or alkenyl ammonium surfactants in which remaining N valences are methyl, hydroxyethyl or hydroxypropyl groups. Suitable examples of amine oxides are the mono $C_8$–$C_{20}$, N-alkyl or alkenyl amine oxides and the propylene-1,3-diamine dioxides in which the remaining N valences are methyl, hydroxyethyl or hydroxypropyl substituents.

The detergent compositions can comprise from 1 to 70% w/w, suitably from 1 to 20% w/w of surfactant. Mixtures of anionic with nonionic or zwitterionic surfactant types are preferred.

Suitable inorganic peroxygen bleach precursors which act as a source of a peroxygen compound e.g. hydrogen peroxide, include sodium perborate mono- and tetrahydrate, sodium percarbonate, sodium persilicate and the clathrate $4Na_2SO_4 \cdot 2H_2O_2 \cdot 1\ NaCl$.

If clathrate materials are used as the peroxygen bleach precursor a separate source of alkalinity will be required and for stability reasons these are preferably stored separately from the hydrogen peroxide source. The precursor compound (ii) acting as the hydrogen peroxide source can be present in an amount of from 1 to 40% w/w suitably from 5 to 35% by weight, preferably from 10 to 30% by weight of the total composition.

In the detergent compositions of the present invention the molar ratio of peroxygen compound e.g. hydrogen peroxide generated from a bleach precursor to bleach activator is suitably greater than 1.5:1, preferably at least 2.0. Under the usage conditions encountered in domestic laundry practice, the molar ratio of bleach precursor to bleach activator is generally greater than 5.0:1 and is most preferably greater than 10:1.

Suds suppressing agents which are useful in the detergent compositions of the invention are suitably selected from silicone, wax, vegetable and hydrocarbon oil and phosphate ester varieties. Suitable silicone suds controlling agents include polydimethylsiloxanes having a molecular weight in the range from 200 to 200,000 and a kinematic viscosity in the range from 20 to 2,000,000 $mm^2/s$ (cSt), preferably from 3000 to 30,000 $mm^2/s$ (cSt), and mixtures of siloxanes and hydrophobic silanated (e.g. trimethylsilanated) silica having a particle size in the range from 10 to 20 millimicrons and a specific surface area above 50 $m^2/g$. Suitable waxes include microcrystalline waxes having a melting point in the range from 65° C. to 100° C., a molecular weight in the range from 4,000–10,000 and a penetration value of at least 6, measured at 77° C. by ASTM-D1321 and also paraffin waxes, synthetic waxes and natural waxes. Suitable phosphate esters include mono- and/or di-$C_{16}$–$C_{22}$ alkyl or alkenyl phosphate esters, and the corresponding mono- and/or di alkyl or alkenyl ether phosphates containing up to 6 ethoxy groups per molecule.

Suds suppressors are normally present in an amount from 0.01 to 5% w/w of the total composition depending upon the type of suds suppressor used, and is preferably from 0.1 to 2% w/w.

A highly preferred component of detergent compositions in accordance with the invention is one or more detergent builder salts which may comprise up to 90% of the composition, more typically from 10 to 70% by weight thereof. Suitable detergent builder salts useful herein can be of the polyvalent inorganic and polyvalent organic types or mixtures thereof. Examples of suitable water-soluble, inorganic alkaline detergent builder salts include the alkali metal carbonates, borates, phosphates, pyrophosphates, tripolyphosphates and bicarbonates.

Examples of suitable organic alkaline detergency builder salts are water-soluble polycarboxylates such as the salts of nitrilotriacetic acid, lactic acid, glycollic acid and ether derivatives thereof; succinic acid, malonic acid, (ethylenedioxy)diacetic acid, maleic acid, diglycollic acid, tartaric acid, tartronic acid and fumaric acid; citric acid, aconitic acid, citraconic acid, carboxymethyloxysuccinic acid, lactoxysuccinic acid, and 2-oxy-1,1,3-propane tricarboxylic acid; oxydisuccinic acid, 1,1,2,2-ethane tetracarboxylic acid, 1,1,3,3-propane tetracarboxylic acid and 1,1,2,3-propane tetracarboxylic acid; cyclopentane cis, cis, cistetracarboxylic acid, cyclopentadiene pentacarboxylic acid, 2,3,4,5-tetrahydrofuran-cis, cis, cis-tetracarboxylic acid, 2,3,4,5-tetrahydrofuran-cis, cis, cis-tetracarboxylic acid, 2,5-tetrahydrofuran-cis-dicarboxylic acid, 1,2,3,4,5,6-hexanehexacarboxylic acid, mellitic acid, pyromellitic acid and the phthalic acid derivatives.

Water-insoluble detergent builders can also be used. A specific example of such builders are the zeolites especially the sodium type A zeolite typified by SASIL (Registered Trade Mark).

Mixtures of organic and/or inorganic builders can also be used.

Chelating agents, soil suspending and anti-redeposition agents, optical brightening agents, enzymes, colours and perfumes may also be added to the detergent composition.

Chelating agents that can be incorporated include citric acid, nitrilotriacetic and ethylene diamine tetra acetic acids and their salts, organic phosphonate derivatives such as those disclosed in U.S. Pat. Nos. 3,213,030, 3,433,021, 3,292,121 and 2,599,807 and carboxylic acid builder salts such as those disclosed in U.S. Pat. No. 3,308,067. The chelating agents can be present in amounts ranging from 0.1 to 3%, suitably from 0.2 to 2% by weight of the total composition.

The detergent compositions containing the bleach activators of the present invention may contain, in addition, minor conventional additives such as fragrances perfumes and the like.

Thus the bleach activators of the present invention should find wide use in detergent compositions which use the inorganic bleach precursors. The fact that these anhydrides activate the bleach precursors at relatively lower temperatures e.g. from 20°–60° C. than those used hitherto should enable a considerable energy saving to be achieved, when the detergents are used. The present invention is further illustrated with reference to the accompanying Examples.

EXAMPLE 1

Preliminary washing/bleaching tests were carried out on standard stained cloth swatches (EMPA* red wine 1"×4") in a beaker maintained at a constant temperature of 40° C. using the base detergent powder composition (Table 1) and the various bleach activators described in Tables 2 and 3.

*The following Examples were carried out using a testing technique prescribed by the Swiss Federal testing agency, Eidgenössische Material Prüsungs und Versuchsanstalt CH-9001; St. Gallen; Unterstrasse; PO Box 977; Switzerland.

2.4 g of base detergent plus 0.45 g of sodium perborate tetrahydrate plus bleach activator (0.15 g, 5.0% w/w) as described in Tables 2 and 3 were added to 600 ml of tap water at 40° C. having a hardness of about 290 ppm of calcium carbonate. Red wine stained swatches were added, then the composition stirred for 30 minutes at 40° C. after which the swatches were removed, rinsed in tap water and dried at 24° C. The stain removal achieved by each bleach activator was assessed visually, using standard lighting conditions (ICS-Texocon Multilight Cabinet, D65) and compared to the stain removal achieved by TAED (10) and that of a blank run (using perborate alone having a value 0), in which no bleach activator was used, and a rating awarded. This is hereafter identified as "EMPA".

TABLE 1

|  | % |
|---|---|
| Linear sodium benzene sulphonate (mean length of alkyl chain $C_{11.5}$) | 8.0 |
| Ethoxylated tallow alcohol (14 EO) | 2.9 |
| Sodium soap (chain length $C_{12}$–$C_{16}$: 13–26% $C_{18}$–$C_{22}$: 74–87%) | 3.5 |
| Sodium triphosphate | 43.8 |
| Sodium silicate ($SiO_2$:$Na_2O$ = 3.3:1) | 7.5 |
| Magnesium silicate | 1.9 |
| Carboxymethylcellulose | 1.2 |
| Sodium ethylenediaminetetraacetate | 0.2 |
| Sodium sulphate | 21.2 |
| Water | 9.8 |
|  | 100 |

TABLE 2

Visual Rating of Stain Removal
2-Methyl (4H)3,1-benzoxazin-4-one Derivatives
(Beaker, Red Wine Cloths, 30 Minutes, 40° C., 5% Activator)

| R | X | Method of Preparation | Visual Rating |
|---|---|---|---|
| 2-Methyl | H | ref 1 | 11 |
| 2-Chloromethyl | H | ref 2 | 11 |
| 2-Dichloromethyl | H | ref 2 | 3 |
| 2-Trichloromethyl | H | ref 2 | 3 |
| 2-Methoxymethyl | H | ref 2 | 11 |
| 2-Amino | H | ref 3 | 2 |
| 2-Dimethylamino | H | ref 4 | 11 |
| 2-Acetyl | H | ref 2 | 10 |
| 2-Ethoxy | H | ref 2 | 7 |
| 2-Methyl | 6,7-Dimethoxy | ref 5 | 11 |
| 2-Methyl | 7-Chloro | ref 5 | 11 |
| 2-Methyl | 6-Chloro | ref 5 | 11 |
| 2-Methyl | 8-Methyl | ref 5 | 11 |
| 2-Methyl | 6-Methyl | ref 5 | 11 |
| 2-Methyl | 5-Methyl | ref 5 | 11 |
| 2-Methyl | 6-Acetoxy | ref 6 | 9 |
| 2-Methyl | 6-Hydroxy | ref 7 | 8 |
| 2-Methyl | 7-Nitro | ref 5 | 10 |

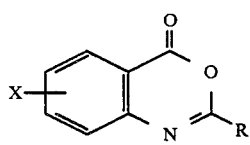

TABLE 3

Visual Rating of Stain Removal
(Beaker, Red Wine Cloths, 30 Minutes, 40° C., 5% Activator)

| Activator | Method of Preparation | Visual Rating |
|---|---|---|
| (pyridine structure) | ref 5 | 10 |
| (imidazole structure) | ref 5 | 9 |
| (isoxazolinone structure) | ref 8 | 7 |
| (dihydrooxazine structure) | ref 9 | 10 |

References

1. L. A. Errede, J. Org. Chem., 1976, 41, 1763; U.S. Pat. No. 3,989,698.
*2. GB-A-1389128;
3. K. Lempert and G. Doleschall, Monatsh, 1964, 95(3), 950.
4. G. V. Boyd and R. L. Monteil, J. Chem. Soc. Perkin 1., 1978, 1338.
*5. D. R. Desai, V. S. Patel, and S. R. Patel, J. Indian Chem. Soc., 1966, 43(5), 351.
6. See Synthesis below.
7. See Synthesis below.
8. M. Crawford and W. T. Little, J. Chem. Soc., 1959, 729.
9. C. N. C. Drey and R. J. Ridge, J. Chem. Soc. Perkin 1, 1980, 378.

*references 2 and 5 contain general methods of preparation which was adapted to prepare each compound using the conditions given and the appropriate starting materials.

Synthesis of Bleach Activators

1. Preparation of 6-Acetoxy-2-Methyl (4H)3,1-benzoxazin-4-one.

5-Hydroxy anthranilic acid (30.6 g, 0.2 mol) was refluxed in acetic anhydride (100 ml) for 3 hours. On cooling a solid precipitated which was collected by filtration, washed with diethyl ether and dried. 6-Acetoxy-2-methyl (4H)3,1-benzoxazin-4-one was isolated as off-white crystals (11.2 g, 26%).

2. Preparation of 6-Hydroxy-2-Methyl (4H)3,1-benzoxazin-4-one.

Sodium hydroxide (4 g. 0.1 mol) was dissolved in water (4 ml) and methanol (50 ml). The 6-acetoxy-2-methyl (4H)3,1-benzoxazin-4-one (8.2 g, 0.04 mol), prepared above, in methanol (30 ml) was added, and the mixture refluxed for 3 hours. The solvent was removed by evaporation and the resulting sodium salt dissolved in water and acidified with hydrochloric acid. 5-Hydroxy N-acetyl anthranilic acid was collected as a beige solid and dried under vacuum. The dry solid (7.8 g, 0.04 mol) was then dissolved in dry THF (100 ml) and added to dicyclohexylcarbodiimide (8.24 g, 0.04 mol) in dry THF (50 ml). The mixture was stirred at room temperature for 18 hours and the insoluble urea removed by filtration. The filtrate was evaporated to dryness to give 6-hydroxy-2-methyl (4H)3,1-benzoxazin-4-one (2.7 g, 38%).

EXAMPLE 2

Further washing/bleaching tests were carried out on standard stained cloth swatches (EMPA red wine stained 2"×6") using the base detergent powder composition (Table 1) and the various bleach activators described in Table 4 in a terg-o-tometer. The terg-o-tometer was maintained at a constant temperature of 40° C. and operated at 75 rpm.

4 g of base detergent plus 0.75 g sodium perborate tetrahydrate plus bleach activator (0.25 g, 5.0% w/w) as described in Table 4 were added to one liter of tap water at 40° C., having a hardness of about 290 ppm as calcium carbonate. Red wine swatches were added, then the composition agitated for 20 minutes at 40° C: after which the swatches were removed, rinsed in tap water and dried at 24° C. The reflectance of the swatches were taken before and after using an ICS Micromatch reflectometer and the percentage stain removal (% SR) calculated by applying the following formula:

$$\% \, SR = \frac{L \, \text{sample} - L \, \text{redwine}}{L \, \text{sample} - L \, \text{redwine}} \times 100$$

Where L is a whiteness parameter generated by the ICS Microwatch reflectometer (black=0 and white=100). Three replicates were run and the average of the results is quoted.

TABLE 4

Percentage Stain Removal
2-Methyl (4H)3,1-benzoxazin-4-one Derivatives
(Terg-o-Tometer, Red Wine Cloths,
20 Minutes, 40° C., 5% Activator)

| R | X | % Stain Removal |
|---|---|---|
| 2-Methyl | H | 83.7 |
| 2-Methyl | 8-Methyl | 71.5 |
| 2-Methyl | 6-Methyl | 82.4 |
| 2-Methyl | 5-Methyl | 77.5 |
| 2-Methyl | 6-Chloro | 81.5 |
| 2-Methyl | 7-Chloro | 80.6 |
| 2-Methyl | 6,7-Dimethoxy | 70.5 |
| 2-Methyl | 7-Nitro | 77.0 |
| 2-Chloromethyl | H | 81.9 |
| 2-Dichloromethyl | H | 64.2 |
| 2-Trichloromethyl | H | 70.5 |
| 2-Methoxymethyl | H | 80.8 |
| 2-Dimethylamino | H | 81.1 |
| 2-Acetyl | H | 70.4 |
| TAED | | 77.0 |
| Perborate | | 60.6 |

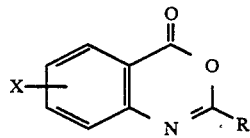

The bleach activator 2-methyl-(4H)3, 1-benzoxazin-4-one (hereafter 2MB4) was selected as a representative example of this series to carry out extensive wasing/bleaching trials.

EXAMPLE 3

A comparison of the percentage stain removal achieved by 2-methyl-(4H)3,1-benzoxazin-4-one (2MB4) and tetraacetyl ethylene diamine (TAED) was made at various temperatures (Table 5).

The washing/bleaching tests were carried out using the same method described in Example 2. In this Example, 4.125 g of base detergent, 0.75 g sodium perborate tetrahydrate plus the bleach activator (0.125 g, 2.5% w/w) and red wine stained swatches were added to one liter of water at various temperatures (Table 5) and agitated for 20 minutes.

The date clearly demonstrate the improved performance of 2MB4 over TAED at the lower temperatures 20° C., 30° C. and 40° C.

TABLE 5

Comparison of 2MB4 with TAED at Various Temperatures
(Terg-o-Tometer, Red Wine Cloths, 20 Minutes, 2.5% Activator)

| Temperature | % Stain Removal 2MB4 | % Stain Removal TAED | % Stain Removal Perborate |
|---|---|---|---|
| 20° C. | 65.9 | 60.0 | 57.4 |
| 30° C. | 75.9 | 69.7 | 64.8 |
| 40° C. | 79.8 | 77.5 | 67.9 |
| 50° C. | 85.9 | 84.9 | 76.3 |
| 60° C. | 90.1 | 88.1 | 84.1 |
| 80° C. | 92.7 | 91.6 | 90.2 |

EXAMPLE 4

A comparison of the percentage stain removal achieved by 2-methyl (4H)3,1-benzoxazin-4-one (2MB4) and tetraacetyl ethylene diamine (TAED) was made at various activator treatment levels (Table 6).

The washing/bleaching tests were carried out using the same method described in Example 2. In this Example, 4 g of base detergent, 0.75 g of sodium perborate tetrahydrate and the activator were added, together with the red wine swatches, to one liter of water at 40° C. and agitated for 20 minutes. The amount of activator used was varied (Table 6) and each time the total made up to 5 g using sodium sulphate.

The results indicate that 2MB4 out-performs TAED at different levels of activator treatment. Addition of more TAED does not lead to significantly greater stain removal than those achieved by lower levels of 2MB4.

TABLE 6

Comparison of 2MB4 with TAED at Various Treatment Levels
(Terg-o-Tometer, Red Wine Cloths, 20 Minutes, 40° C.)

| % Activator | % Stain Removal 2MB4 | % Stain Removal TAED |
|---|---|---|
| 0.0 | 66.5 | 66.5 |
| 1.0 | 76.9 | 73.2 |
| 2.5 | 81.1 | 77.3 |
| 5.0 | 85.5 | 82.0 |

EXAMPLE 5

Washing/bleaching tests were carried out on standard stained tea swatches (EMPA 2"×6") and the percentage stain removal of 2-methyl (4H)3,1-benzoxazin-4-one (2MB4) and tetraacetyl ethylene diamine (TAED) at different temperatures and treatment levels were measured (Table 7).

The tests were carried out using the same method as that described in Example 2. However, in this Example, tea stained swatches were used and the results taken after 30 minutes. The temperatures and the amount of activator used are described in Table 7.

These results again demonstrate the improved performance of 2MB4 over TAED.

TABLE 7

Comparison of 2MB4 with TAED (Tea Stained Cloth)
(Terg-o-Tometer, 30 Minutes)

| Activator | % Stain Removal 30° C. | % Stain Removal 40° C. |
|---|---|---|
| 2% 2MB4 | 83.7 | 90.8 |
| 2% TAED | 79.1 | 88.3 |
| 3% 2MB4 | 86.1 | 91.5 |
| 3% TAED | 82.2 | 91.3 |
| Perborate | 72.5 | 81.8 |

EXAMPLE 6

A comparison of the percentage stain removal of 2-methyl (4H)3,1-benzoxazin-4-one (2MB4) with other bleach activators, tetracetyl ethylene diamine (TAED), isononanoyl oxybenzene sulphonate (ISONOBS), magnesium monoperoxyphthalate hexahydrate (ex-Interox H48), and diperoxydodecanedioic acid (DPDDA), was carried out (Table 8).

The bleach activators were compared on an equal activity basis, and sufficient of the supplied commercial activator was added to provide a level of 2% activity. The actual weights of bleach activator, as supplied by the manufacturer, used in the washing tests are shown in Table 8. The total compositions were made up to 5 g using sodium sulphate.

The tests were performed using the same method as that described in Example 2. In this Example 3.4 g of base detergent, 0.75 g of sodium perborate tetrahydrate, the bleach activator, and red wine swatches were added to one liter of tap water at 40° C. and agitated for 20 minutes.

The bleaching performance of 2MB4 was more effective than all the other bleach activators under these conditions except DPDDA.

However, further washing tests which compare 2MB4 and DPDDA on an equal available oxygen basis (Example 7) and on an equal weight basis (Example 8) indicate that 2MB4 does out-perform DPDDA under other conditions.

TABLE 8

(Equal Activity)
(Terg-o-Tometer, Red Wine Cloths, 20 Minutes)

| Activator | % Stain Removal | Weight of Activator Used |
|---|---|---|
| 2MB4 | 75.0 | 0.1 g |
| TAED | 73.6 | 0.1 g |
| ISONOBS | 71.1 | 0.1 g |
| H48 | 68.6 | 0.1 g |
| DPDDA | 77.1 | 0.83 g |
| Perborate | 66.3 | 0.0 g |

EXAMPLE 7

Washing tests were carried out to compare 2-methyl (4H)3,1-benzoxazin-4-one (2MB4) with diperoxydodecanedioic acid (DPDDA) on an equal available oxygen basis (Table 9).

The tests were performed using the same method as that described in Example 2. In this Example 3.05 g of base detergent, 0.75 g of sodium perborate tetrahydrate, the bleach activator, and the red wine swatches were added to one liter of tap water at 40° C. and agitated for 20 minutes. Sufficient bleach activator was used to provide an available oxygen content of $1.096 \times 10^{-3}$ mol. The actual weights of bleach activator, as supplied by the manufacturer, used in the washing tests are shown in Table 9. The total compositions were made up to 5 g using sodium sulphate.

The data demonstrate that 2MB4 does out-perform DPDDA under these conditions.

TABLE 9

Comparison of 2MB4 with DPDDA
(Equal Available Oxygen)
(Terg-o-Tometer, red Wine Cloths, 20 Minutes, 40° C.)

| Activator | % Stain Removal | Weight of Activator Used |
|---|---|---|
| 2MB4 | 85.4 | 0.125 g |
| DPDDA | 83.8 | 1.129 g |
| TAED | 81.8 | 0.125 g |

EXAMPLE 8

A comparison of the percentage stain removal of 2-methyl (4H)3,1-benzoxazin-4-one (2MB4) and diperoxydodecanedioic acid (DPDDA) was made on an equal weight basis (Table 10).

The tests were carried out using the same method as that described in Example 2. In this Example 4.125 g of base detergent, 0.75 g of sodium perborate tetrahydrate, the bleach activator (0.125 g, 2.5% w/w), and the red wine swatches were added to one liter of tap water at 40° C. and agitated for 20 minutes.

Again, 2MB4 clearly out-performs DPDDA under these conditions.

TABLE 10

(Equal Weight)
(Terg-o-Tometer, Red Wine Cloths, 20 Minutes, 2.5% Activator)

| Activator | % Stain Removal | Weight of Activator Used |
|---|---|---|
| 2MB4 | 75.2 | 0.125 g |
| DPDDA | 62.5 | 0.125 g |
| Perborate | 61.5 | 0.0 g |

EXAMPLE 9

Washing/bleaching tests were carried out to compare 2-methyl (4H)3,1-benzoxazin-4-one (2MB4) with isononanoyl oxybenzene sulphonate (ISONOBS) under washing conditions used in the USA (Table 11).

1.2 g of base detergent, 0.15 g of sodium perborate tetrahydrate and the bleach activator (0.15 g, 10% w/w) were added to one liter of tap water at 25° C. Red wine stained swatches were added and the composition agitated for 20 minutes at 25° C. after which the swatches were removed, rinsed in tap water and dried at 24° C. The percentage stain removal was then measured and calculated in the same way as described in Example 2.

The data in Table 11 demonstrates the improved performance of 2MB4 over ISONOBS under these conditions. The difference in stain removal is even more pronounced than in the tests carried out under washing conditions used in Europe (Table 8).

TABLE 11

Comparison of 2MB4 with ISONOBS
(USA Washing Conditions)
(Terg-o-Tometer, Red Wine Cloths,
20 Minutes, 25° C., 10% Activator)

| Activator | % Stain Removal |
|---|---|
| 2MB4 | 70.1 |
| ISONOBS | 63.3 |
| Perborate | 60.7 |

We claim:

1. A detergent composition in aqueous solution comprising
    (i) a surfactant selected from anionic, nonionic, zwitterionic and cationic surfactants and mixtures thereof,
    (ii) a precursor compound capable of giving rise to a peroxygen compound in the presence of water,
    (iii) a bleach activator capable of enhancing the bleaching activity of the peroxygen compound so formed,
    (iv) a suds suppressing agent and
    (v) a detergent builder, characterised in that the bleach activator comprises one or more cyclic tertiary nitrogen compounds of the generic formula

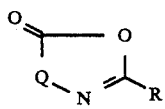
(I)

wherein Q is an organic divalent grouping such that Q and N together with the carbonyl and oxygen functions in the compound form one or more cyclic structures and R is H an alkyl, alkaryl, aryl, aralkyl, alkoxyl, haloalkyl, amino alkyl, amino, carboxylic or a carbonyl-containing groups, said activator being at least partially soluble in water.

2. A detergent composition according to claim 1 wherein the bleach activator has the generic formula

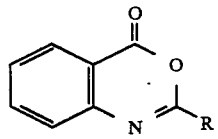
(II)

wherein R has the same significance as in claim 1.

3. A detergent composition according to claim 2 wherein the bleach activator is such that R=CH$_3$ thereby representing 2-methyl-(4H)3,1-benzoxazin-4-one.

4. A detergent composition according to claim 2 wherein the bleach activator is such that R is selected from a dialkylamino group, an acyl group, an alkoxy group, a haloalkyl group and a dialkyl ether group.

5. A detergent composition according to claim 4 wherein R is selected from a dimethyl amino group, an acetyl group, an ethoxyl group, a chloromethyl group, a dichloromethyl group and a dimethyl ether group.

6. A detergent composition according to claim 1 wherein the bleach activator has the generic formula

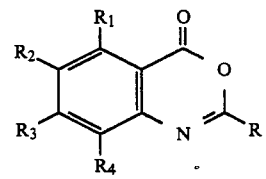
(III)

wherein R has the same significance as in claim 1 and R$_1$, R$_2$, R$_3$ and R$_4$ are the same or different nuclear substituents selected from H, halogen, alkyl, alkenyl, aryl, hydroxyl, alkoxyl, amino, alkylamino, —COOR$_5$ (where R$_5$ is H or an alkyl group), and carbonyl functions.

7. A detergent composition according to claim 6 wherein R$_1$, and R$_4$ are both H, and
    (a) R$_2$=acetoxy and R$_3$=H;
    (b) R$_2$=OH and R$_3$=H;
    (c) R$_2$=R$_3$=alkoxy;
    (d) R$_2$=H and R$_3$=halogen or a haloalkyl group;
    (e) R$_2$=halogen or haloalkyl group and R$_3$=H; or
    (f) R$_2$=H and R$_3$=a carboxyl group.

8. A detergent composition according to claim 7 wherein R$_1$ and R$_4$ are both H, and
    (a) R$_2$=R$_3$=methoxy; or
    (b) R$_2$=H and R$_3$=chlorine 9. A detergent composition according to claim 6 wherein R$_3$=H, and any one of R$_1$, R$_2$ and R$_4$ is a methyl group the other two being H.

10. A detergent composition according to claim 1 wherein the bleach activator has the generic formula

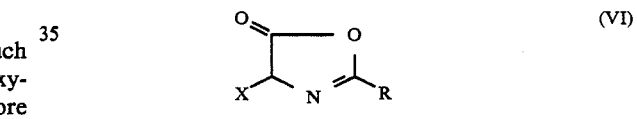

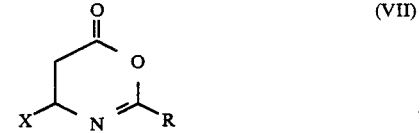

wherein X is H or an organic monovalent group and R has the same significance as in claim 1.

11. A detergent composition according to claim 1 wherein the bleach activator has the generic formula

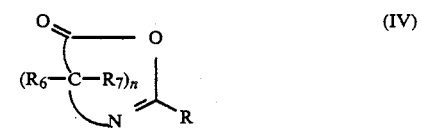

wherein R has the same significance as in claim 1, R$_6$ and R$_7$ are the same or different groups and are any one of the groups denoted by the substituents R$_1$ to R$_4$ in claims 6–8 and n has a value from 1 to 3.

12. A detergent composition according to claim 1 wherein the bleach activator has the generic formula

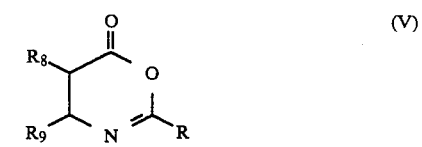

wherein $R_8$ and $R_9$ are the same or different groups and denote any one of the substituents signified by the groups $R_1$ to $R_4$ in claims 6–8.

13. A detergent composition according to claim 12 wherein, $R_8$ and $R_9$ together with the hydrocarbyl carbon atoms bridging the nitrogen and carbonyl functions represent a pyrazole, an imidazole, pyridine pyrimidi or a pyridazine ring.

14. A detergent composition according to claim 1 wherein the bleach activator has the formula

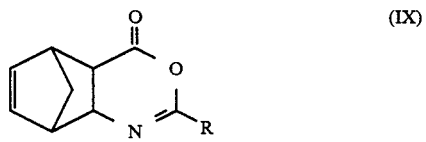

(IX)

wherein R has the same significance as in claim 1.

15. A detergent composition according to claim 1, 2, 3, 4, 5, 6, 7, 8, 9, 10, 11, 12, 13, or 14 claims wherein the precursor compound (ii) acts as a hydrogen peroxide source in the presence of a bleach activator.

16. A detergent composition according to claim 15 wherein the precursor compound (ii) is selected from sodium perborate mono or tetrahydrate, sodium percarbonate, sodium persilicate and the clathrate $4Na_2SO_4$:$H_2O_2$:NaCl.

17. A detergent compound according to claim 15 wherein the precursor compound (ii) is present in an amount from 1 to 40% w/w of the total composition.

18. A detergent composition according to claim 15, wherein the molar ratio of hydrogen peroxide generated from the precursor compound to bleach activator therein is greater than 1.5:1.

19. A detergent composition according to claim 15 wherein the amount of surfactant (i) ranges from 1 to 70% w/w of the total composition.

20. A detergent composition according to claim 15 claims wherein the amount of suds suppressing agent (iv) in the formulation ranges from 0.01 to 5% w/w of the total composition.

21. A detergent composition according to claim 15 wherein the detergent builder (v) is a salt which is present in amount of up to 90% w/w of the total composition.

* * * * *

UNITED STATES PATENT AND TRADEMARK OFFICE
CERTIFICATE OF CORRECTION

PATENT NO. : 4,966,723
DATED : October 30, 1990
INVENTOR(S) : STEPHEN R. HODGE et al It is certified that error appears in the above-identified patent and that said Letters Patent is hereby corrected as shown below:

Col. 6, l. 55, "The present" should start a new paragraph

Col. 7, l. 4, after "Switzerland." insert --- This is hereafter identified as "EMPA"

Col. 7, l. 20, strike this line as it should have appeared in line 4

Claim 13, l. 4, after "pyridine" insert a comma (,) and correct the spelling of "pyrimidine".

Claim 15, l. 2, after "14" strike "claims"

Claim 20, l. 2, strike "claims"

Signed and Sealed this

Twenty-first Day of July, 1992

Attest:

DOUGLAS B. COMER

*Attesting Officer*   Acting Commissioner of Patents and Trademarks